US006884880B2

United States Patent
Gupta et al.

(10) Patent No.: US 6,884,880 B2
(45) Date of Patent: Apr. 26, 2005

(54) PROCESS FOR THE PREPARATION OF 9-β-ANOMERIC NUCLEOSIDE ANALOGS

(75) Inventors: Pranab K. Gupta, West Bloomfield, MI (US); Stephen A. Munk, Northville, MI (US)

(73) Assignee: Ash Stevens, Inc., Detroit, MI (US)

(*) Notice: Subject to any disclaimer, the term of this patent is extended or adjusted under 35 U.S.C. 154(b) by 0 days.

(21) Appl. No.: 10/225,032

(22) Filed: Aug. 21, 2002

(65) Prior Publication Data

US 2004/0039190 A1 Feb. 26, 2004

(51) Int. Cl.$^7$ .............. A61K 31/70; C07H 1/00; C07H 19/073

(52) U.S. Cl. .............. 536/27.3; 536/27.11; 536/22.1; 536/55.3; 536/24.5; 536/25.3; 536/27.81; 536/23.1; 536/28.5; 536/28.1; 536/28.52; 536/28.55; 536/26.23; 536/25.32; 536/25.31; 536/26.6; 536/26.71; 536/27.6; 536/27.3; 536/28.4; 514/43; 514/45; 435/6; 435/89; 544/277

(58) Field of Search .............. 536/27.3, 27.11, 536/22.1, 55.3, 24.5, 25.3, 27.81, 23.1, 28.5, 28.1, 28.52, 28.55, 26.23, 25.32, 25.31, 26.6, 26.71, 27.6, 28.4, 27.8, 26.1; 514/43, 45; 435/6, 89; 544/277

(56) References Cited

U.S. PATENT DOCUMENTS

| 4,189,581 A | * | 2/1980 | Scharwaechter et al. | .... 544/324 |
| 4,760,137 A | | 7/1988 | Robins et al. | |
| 5,459,255 A | | 10/1995 | Cook et al. | |
| 5,821,357 A | * | 10/1998 | Chou et al. | ................ 536/55.3 |

FOREIGN PATENT DOCUMENTS

EP 351795 1/1990

OTHER PUBLICATIONS

J. Med. Chem. 33, 978 (1990).
J.A.C.S. 105, 4059 (1983).
Robins et al., J.A.C.S. 106 6379 (1984).
J. Med. Chem. 37, 821 (1994).
J. Med. Chem. 34, 1647 (1991).
Ikehara, M., et al., J. Amer. Chem. Soc. 87:3 (1965).
Communications to the Editor, vol. 85, p. 2344 (1963).
Furukawa, Y., et al., Chem. Pharm. Bull. 16(6) 1076–1080 (1968).
Cancer Res. 42, 3911 (1982).
Suhadolnik, R.J., Nucleoside Antibiotics: New York Wiley-–Interscience.
J. Med. Chem. 35, 397 (1992).

* cited by examiner

Primary Examiner—James O. Wilson
Assistant Examiner—Devesh Khare
(74) Attorney, Agent, or Firm—Ian C. McLeod

(57) ABSTRACT

A process for substantially enhancing the regio and stereoselective synthesis of 9-β-anomeric nucleoside analogs is described. The introduction of the sugar moiety onto a 6-substituted purine base was preformed so that only the 9-β-D- or L-purine nucleoside analogs were obtained. This regio and stereoselective introduction of the sugar moiety allows the synthesis of nucleoside analogs and in particular 2'-deoxy, 3'-deoxy, 2'-deoxy-2'-β-fluoro and 2',3'-dideoxy-2'-β-fluoro purine nucleoside analogs in high yield without virtually any formation of the 7-positional isomers. The compounds are drugs or intermediates to drugs.

22 Claims, No Drawings

PROCESS FOR THE PREPARATION OF 9-β-ANOMERIC NUCLEOSIDE ANALOGS

BACKGROUND OF THE INVENTION

(1) Field of the Invention

The present invention relates to a process for the preparation of 9-beta-anomeric nucleoside analogs. In particular the present invention relates to the preparation of 2'-deoxy, 3'-deoxy, 2'-deoxy-2'-β-fluoro and 2',3'-dideoxy-2'-fluoro purine nucleoside analogs. The process avoids the formation of 7-position isomers because of a protective group in the 6-position.

(2) Description of Related Art

Prior glycosylation procedures in which the 2-deoxy-β-D- or L-ribofuranosyl (2-deoxy-β-D- or L-erythro-pentofuranosyl), 3-deoxy-β-D- or L-ribofuranosyl (3-deoxy-β-D- or L-erythro-pentofuranosyl), 2-deoxy-2-fluoro-β-D- or L-arabinofuranosyl (2-deoxy-2-fluoro-β-D- or L-threo-pentofuranosyl), 2,3-dideoxy-2-fluoro-β-D- or L-arabinofuranosyl (2,3-dideoxy-2-fluoro-β-D- or L-threo-pentofuranosyl) or the β-D- or L-arabinofuranosyl moiety is introduced into an aglycon moiety invariably provide anomeric mixtures as well as positional isomers which results in very low yield of the desired nucleoside. In view of these difficulties, a four step deoxygenation procedure using phenoxythiocarbonylation was developed to obtain the 2'-deoxy nucleosides (J.A.C.S. 1983, 105, 4059) or the 2,3-dideoxy-2-fluoro-β-D-arabinofuranosyl nucleosides (J. Med. Chem. 1990, 33, 978). The 3'-deoxyadenosine (Cordycepin) was also made starting from adenosine via an 2',3'-anhydroadenosine route followed by the epoxide ring opening (Synthesis. 1985, 1108).

What all these procedures lack, however, is an improved process that does not require the availability of the pre-formed nucleoside and also is applicable in the presence of halo heterocyclic (preferably 2-halo) derivatives, which are the most useful for further nucleophilic displacements. Later on, Robins et al. (J.A.C.S. 1984, 106, 6379) developed a stereospecific sodium salt glycosylation procedure for the synthesis of 2'-deoxy nucleosides. This procedure eliminates the formation problem of the α-anomeric nucleoside but the positional isomer question (N-9 and N-7) remained to be solved. Moreover the tedious silica gel column purification between the two very similar positional isomers is unacceptable for large scale preparation of 2'-deoxy nucleosides. The sodium salt glycosylation procedure was also explored for the synthesis of 2'-F-ara-ddA (J. Med. Chem. 1994, 37, 821) and again the separation of the isomers and a suitable large scale method remained to be solved. Marquez et al. had also reported (J. Med. Chem. 1990, 33, 978 and 1991, 34, 1647) the coupling of purine or 6-chloropurine with the 2'-β-fluoro-bromo sugar to obtain an expected mixture of four isomeric nucleosides and the time consuming purification of the reaction mixture through silica gel column chromatography. Moreover for the synthesis of adenosine type nucleosides (having the 6-amino group in purine moiety), the treatment of the 6-chloro blocked nucleoside with methanolic ammonia at elevated temperature and pressure to obtain the 6-amino purine nucleoside is the method of choice. This conversion often requires to carry out the reaction in steel bomb or sealed tube at elevated temperature. Therefore a more expedient and flexible approach that provided a more simplified process to the target biologically active nucleosides is needed.

Related art: U.S. Pat. No. 4,760,137 to Robins et al; Ikehara, M, et al., J. Amer. Chem. Soc. 87:3 (1965); Communications to the Editor, Vol. 85, pg. 2344 (1963); U.S. Pat. No. 5,459,255 to Cook et al.; Furukawa, Y., et al., Chem. Pharm. Bull. 16(6)1076–1080 (1968).

OBJECTS

It is therefore an object of the present invention to provide a novel process for the preparation of 9-β-anomeric nucleoside analogs. In particular, it is an object of the present invention to provide a relatively economical process which produces the analogs in high yield. These and other objects of the present invention will become increasingly apparent from the following description.

SUMMARY OF THE INVENTION

The present invention relates to a process for producing a protected 9-substituted purine nucleoside (I) of the formula:

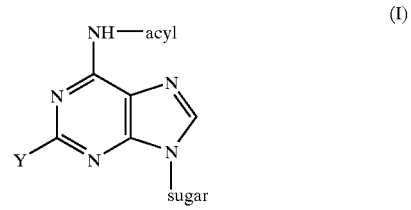

wherein acyl contains 1 to 14 carbon atoms and is a non-reactive group which comprises:

reacting a salt of an anionic 6-substituted purine (II) of the formula:

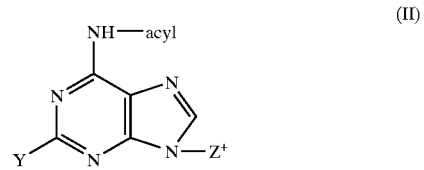

wherein Z is Na or K with an O— protected activated sugar in a non-reactive solvent for (II) to produce (I), essentially without formation of a 7-position analog.

The present invention particularly relates to a process for producing a protected 9-substituted purine nucleoside (I) of the formula:

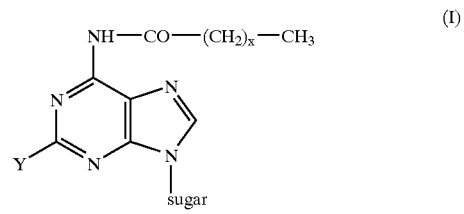

wherein x is 4 to 12 and Y is a non-interfering moiety, preferably selected from the group consisting of H, Cl, F, Br, $OCH_3$, $NH_2$, NHR, wherein R is a non-reactive group which comprises:

(a) reacting a salt of an anionic 6-substituted purine (II) of the formula:

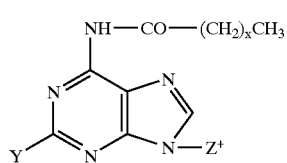

(II)

wherein Z is Na or K.

(b) with an O— protected activated sugar in a non-reactive solvent for (II) to produce (I), essentially without formation of a 7-position analog. R preferably contains 1 to 20 carbon atoms, which can be substituted, including alkoxy, alkyl, carboxylic, heterocyclic and aryl groups. Preferably x is 5. Preferably the activated sugar is selected from the group consisting of a pentafuranose, 2-deoxypentofuranose and a substituted 2-deoxypentafuranose with protected OH groups. Preferably the solvent is anhydrous tetrahydrofuran. Preferably (II) is produced by reacting a compound (III) of the formula

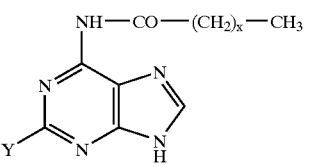

(III)

with a base, particularly potassium or sodium hexamethyl disalazide (KHMDS). Preferably compound (III) is prepared by reacting adenine with an anhydride of the formula:

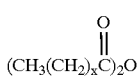

(IV)

where x is 4 to 12. Preferably x is 5 to 9. Preferably the sugar is a 1-halosugar.

DESCRIPTION OF PREFERRED EMBODIMENT

The present invention, which overcomes the difficulties and shortcomings of the previous procedures, concerns a process for producing the 9-β-D- or L-purine nucleosides, including the adenosines which are 2'-deoxyadenosines, 3'-deoxyadenosines, 2'-β-F-2'-deoxyadenosines 2'β-F-2',3'-dideoxyadenosines and 2-F-ara-A compounds, and ara-A comprising glycosylating a potassium salt of a purine compound having the general formula with the 1-chloro-2-deoxy-3,5-di-O-p-toluoyl-α-D- or L-erythropentafuranose, 1-chloro-3-deoxy-2,5-di-O-benzoyl-β-D- or L-

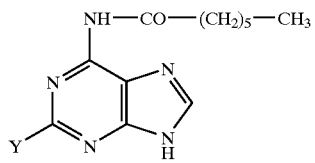

1. Y = H
2. Y = Cl
3. Y = F erythropentafuranose, 2-Deoxy-2-fluoro-3,5-di-O-benzoyl-α-D- or L-arabinofuranosyl bromide; 2,3-dideoxy-2-fluoro-5-O-p-toluoyl-α-D- or L-arabinofuranosyl chloride and 2,3,5-tri-O-benzyl-α-D- or L-arabinofuranosyl bromide isolating respectively the resulting 9-(2-deoxy-3,5-di-O-p-toluoyl-β-D- or L-erythropentofuranosyl)purine having the general formula 5

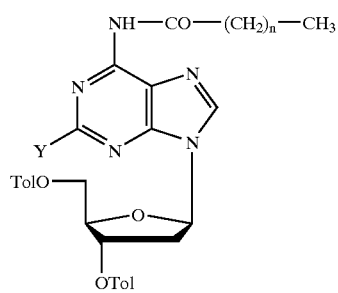

5 where Y is H, Cl or F.

9-(3-deoxy-2,5-di-O-benzoyl-β-D- or L-erythropentofuranosyl)purine having the formula 6

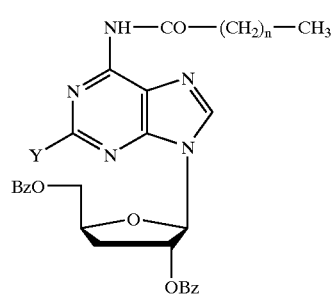

6 wherein Y is H, Cl or F, 9-(2-deoxy-2-fluoro-3,5-di-O-benzoyl-β-D- or L-arabinofuranosyl)purine having the formula 7

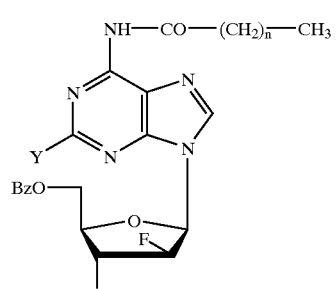

7 wherein Y is H, Cl or F, 9-(2,3-dideoxy-2-fluoro-5-O-p-toluoyl-β-D-arabinofuranosyl)purines having formula 8

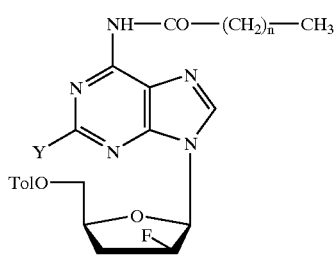

wherein Y is H, Cl or F,

2-Fluoro-9-(2,3,5-tri-O-benzyl-β-D-arabinofuranosyl)purine having formula 9

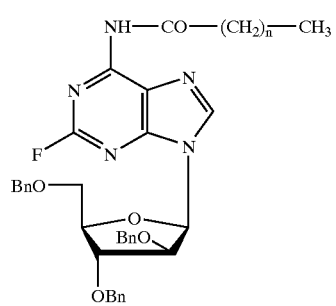

and subjecting the above examples under deblocking conditions with sodium methoxide to obtain respectively the corresponding final nucleosides 2'-deoxyadenosines having the formula 10 (Y=H is 10a, Y=Cl is 10b)

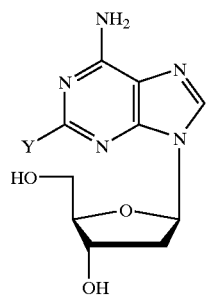

10a, Y = H
10b, Y = Cl

3'-deoxyadenosines having the formula 11 (Y=H is 11a; Y=Cl is 11b)

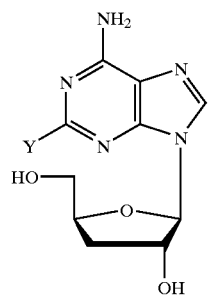

11a, Y = H
11b, Y = Cl 9-(2-deoxy-2-fluoro-β-D- or L-arabinofuranosyl)adenines having the formula 12 (Y=H is 12a, Y=Cl is 12b)

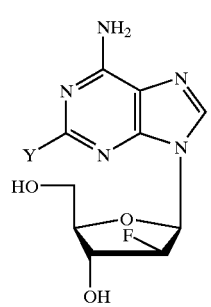

12a, Y = H
12b, Y = Cl 9-(2,3-dideoxy-2-fluoro-β-D- or L-arabinofuranosyl)adenines having the general formula 13 (Y=H is 13a, Y=Cl is 13b)

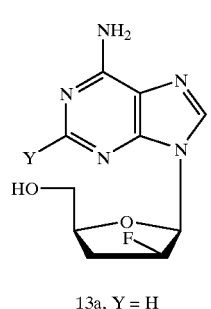

13a, Y = H
13b, Y = Cl and 2-Fluoro-9-β-D- or L-arabinofuranosyladenine (Fludarabine) having the formula 14, after removing the protecting benzyl groups.

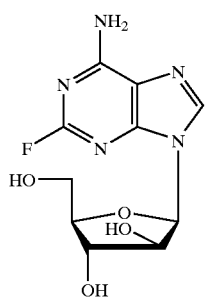

The heptanoylamido purine (1, Y=H ; 2, Y=Cl and 3, Y=F) was prepared by treating the corresponding 6-aminopurine with heptanoic anhydride in N-methylimidazole. The potassium salt of the purine compound is formed in situ by treating a suspension of the purine base in tetrahydrofuran with an organic base potassium bis(trimethylsilyl)amide at −35° C. followed by warming the reaction mixture to room temperature. The glycosylation is carried out at ambient temperature or at reflux temperature until complete, usually within 14 hours. The regiospecificity of the glycosylation step to obtain only the N-9 glycosylated product and the high yield to obtain the β-nucleoside product were both unexpected. The corresponding 6-heptanoylamidopurine not only increased the solubility of the purine base in organic solvent, it also favors the formation of the N-9 glycosylated product and virtually no to a very minor amount of the N-7 glycosylated product was observed as opposed to the most published methods. In most of the cases, the desired N-9 beta glycosylated product formation was rapid and preferentially took place without appreciable anomerization. The N-9 beta glycosylated product is isolated from the reaction mixture in any suitable way, preferably by recrystallisation or by silica gel column purification. The deblocking of the protecting group is accomplished by treating the blocked nucleoside with known in the art sodium methoxide-methanol at reflux temperature to obtain the final nucleoside. Aryl (RO⁻) lower alkyl oxide or ammonia in alcohol will also produce deblocking as is well known in the art. Both the removal of the sugar protecting groups followed by the concomitant hydrolysis of the heptanoylamido group in the aglycon moiety were achieved by treating the blocked nucleoside with sodium methoxide to obtain the corresponding 6-amino purine nucleosides. The products of the method 2'-deoxyadenosine 10a and 2-chloro-2'-deoxyadenosine (Cladribine) 10b are useful cytotoxic agents and are useful for the production of 2'-deoxyadenosine analogs (Cancer Res. 1982, 42, 3911 and EUR. Pat. Appl.; Patent No. 351795), 3'-deoxyadenosine (Cordycepin) 11a; a nucleoside antibiotic having antitumor activity (Suhadolnik, R. J. Nucleoside Antibiotics: New York, Wiley-Interscience) and 2-chloro-3'-deoxyadenosine 11b (a direct analog of Cladribine; a useful cytotoxic agent); 2'-F-2'-deoxy-ara-adenosine 12a and 2-chloro-2'-F-2'-deoxy-ara-adenosine 12b (Clofarabine; a cytotoxic agent against different human cell lines; murine leukemia L 1210 and P388 leukemia in mice; J. Med. Chem. 1992, 35, 397); 2'-F-dideoxy-ara-adenosine 13a (as an anti HIV agent, J. Med. Chem 1990, 33, 978) and 2-chloro-2'-F-dideoxy-ara-adenosine 13b ; and 2-fluoro-ara-adenosine 14 (Fludarabine; the precursor for the synthesis of Fludarabine Phosphate; an FDA approved product for the treatment of refractory chronic lymphocytic leukemia).

EXPERIMENTAL

6-Heptanoylamido purine (1)

Adenine (40.0 g; 296.3 mmol) was suspended in N-methylimidazole (100-ml). To the mechanically stirred mixture under nitrogen atmosphere was added heptanoic anhydride (125 ml; 476.2 mmol) and the mixture was heated at 130° C. to obtain a clear solution. The solution was warmed at 130° C. for 30 minutes and was cooled to 90° C. with stirring. To the stirred solution at 90° C. was added methanol (700 ml) slowly and the mixture was stirred at 40° C. for 5 minutes. The separated solid was collected by filtration and dried at 80° C./0.3 mm Hg/3 h to obtain crude product. This material was crystallized from boiling ethanol (700 ml) to obtain title 1, 51.0 g (70%); m.p. 189–190° C. $^1$H NMR (DMSO-$d_6$): δ 12.30 and 11.87 (brS, 1H, each, $D_2O$ exchangeable, NH), 8.67 (S, 1H, $C_2$—H), 8.46 (S, 1H, $C_8$—H), 2.56 (t, 2H,$CH_2$), 1.66 (m, 2H), 1.31 (m, 6H), 0.87 (t, 3H, $CH_3$) Analysis calculated for $C_{12}H_{17}N_5O$ (247.24): C, 58.28; H, 6.93; N, 28.32. Found: C, 58.21; H, 7.05 N, 28.61.

2-Chloro-6-heptanoylamido Purine (2)

2-Chloroadenine (10.0 g; 59 mmol) was heated with N-methylimidazole (25 ml) and heptanoic anhydride (30 ml; 114.2 mmol) at 130° C. the same way as described for 6-heptanoylamido purine to obtain the 2-chloro-6-heptanoylamido purine 2, 12.0 g (72%); m.p. 269–270° C. $^1$H NMR (DMSO-$d_6$): δ 12.32 and 11.47 (br s, 1H each, $D_2O$ exchangeable; NH), 8.41 (s, 1H, $C_8$—H), 2.51 (t, 2H, $CH_2$), 1.59 (m, 2H, $CH_2$), 1.25 (m, 6H, $CH_2$), 0.83 (t, 3H,$CH_3$), Analysis calculated for $C_{12}H_{16}ClN_5O$ (281.74): C, 51.15; H, 5.72; N, 24.85; Cl, 12.58 Found: C, 51.12; H, 5.76; N, 24.91; Cl, 12.46.

EXAMPLE 1

6-Heptanoylamido-9-(2-deoxy-3,5-di-O-p-toluoyl-β-D-erythro-pentofuranosyl)-purine 1. The heptanoylamido purine 1 (4.94 g; 20 mmol) was suspended in anhydrous THF (55 ml). The mixture was mechanically stirred and cooled to −35° C. under an atmosphere of nitrogen. To the stirred mixture at −35° C. was added 0.5M solution of KHMDS in toluene (40 ml; 20 mmol) dropwise over 5 minutes. The mixture was stirred at −35° C. for 45 minutes; then slowly warmed to room temperature and stirred at room temperature for 30 minutes. Dry powdered 1-chloro-2-deoxy-3,5-di-O-p-toluoyl-α-D-erythropentofuranose (8.58 g; 22 mmol) was added to the stirred mixture portionwise over 10 minutes and the mixture was stirred at ambient temperature for 3 h. The solution was concentrated in vacuo and the residue was taken in methylene chloride (150 ml). The organic layer was washed with water (1×100 ml); 5% $NaHCO_3$ solution (1×50 ml); brine (1×50 ml); dried ($MgSO_4$); filtered and stripped to obtain a crude residue. This material was purified on a silica gel column (3.5×40 cm) using ethyl acetate: hexanes (4:6, v/v) as the solvent. The titled 9-β-D nucleoside was isolated and crystallized from ether: pet-ether (3:1) to yield 7.6 g (64%) product. m.p. 109–110° C. $^1$H NMR ($CDCl_3$): δ 8.79 (br s, 1H, NH), 8.64 (s, 1H, $C_8$—H), 8.34 (s, 1H, $C_2$—H), 6.63 (t, 1H, C'$_1$—H), Analysis calculated for $C_{33}H_{37}N_5O_6$ (599.68): C, 66.09; H 6.22; N, 11.68. Found: C, 66.14; H, 6.16; N, 11.76.

6-Amino-9-(2-deoxy-β-D-erythropentofuranosyl) purine (2'-Deoxyadenosine)10a

2. To a solution of 6-heptanoylamido-9-pentofuranosyl purine (product of 1a; 5.99 g; 10 mmol) in anhydrous methanol (50 ml) at 45° C. was added 25% $CH_3ONa$—

CH$_3$OH (1.6 ml; 7 mmol) all at once and the solution was held at 45° C. with stirring for 10 minutes followed by stirring at room temperature for 1 h. The solution was cooled with stirring (ice-bath) for 1 h. The separated solid was collected by filtration and washed with methanol (1×10 ml). Finally the solid was crystallized from water to yield 1.83 g (73%) of the product 10a; m.p. 188–190° C. [lit-m.p. 187–189° C., and all other physiochemical properties of the titled 2-deoxy adenosine product are identical with 2-deoxy adenosine reported in the literature].

EXAMPLE 2

2-Chloro-6-heptanoylamido-9-(2-deoxy-3,5-di-O-p-toluoyl-β-D-erythero pentofuranosyl)purine a. 2-Chloro-6-heptanoylamido purine 2 (2.81 g, 10 mmol) was suspended in anhydrous THF (28 ml). To the mechanically stirred mixture under nitrogen atmosphere at −30° C. was added 0.5M solution of KHMDS in toluene (20 ml; 10 mmol) and the mixture was stirred at −30° C. for 30 minutes. The mixture was warmed to room temperature and stirred at room temperature for 30 minutes followed by addition of 1-chloro-2-deoxy-3,5-di-O-p-toluoyl-α-D-erythropentofuranose (3.90 g; 10 mmol) portionwise over 5 minutes. The solution was stirred at ambient temperature for 2 h. The solution was concentrated in vacuo and the residue was taken in methylene chloride (100 ml). The organic layer was washed with water (1×50 m), 5% NaHCO$_3$ solution (1×40 ml); brine (1×40 ml); dried (MgSO$_4$); filtered and stripped to obtain a residue. This material was purified on a silica gel column (2.5×35 cm) using ethyl acetate: hexanes (3:7, v/v) as the solvent. Pure fractions were pooled; combined and stripped to obtain a foam. This material was suspended in anhydrous ether and was gently refluxed for 30 minutes and cooled to room temperature. The separated solid was collected by filtration to yield the title compound 3.80 g (60%); m.p. 128–130° C., $^1$HNMR (DMSO-d$_6$): δ 10.98 (br s, 1H, NH), 8.67 (S, 1H, C$_8$—H), 6.521 (t, 1H, peak width 15.2 Hz, C'$_1$H); Analysis calculated for C$_{33}$H$_{36}$N$_5$ClO$_6$ (633.93): C, 62.49; H, 5.72; N, 11.04; Cl5.59. Found: C, 62.44; H, 5.77; N, 11.09 and Cl 5.41.

2-Chloro-6-amino-9-(2-deoxy-β-D-erythro-pentofuranosyl)purine (Cladribine) 10b b. To a suspension of 2-chloro-6-heptanoylamido-9-pentofuranosyl purine (product of 2a, 3.60 g; 5.68 mmol) in anhydrous methanol (30 ml) at 50° C. under nitrogen atmosphere was added 25% CH$_3$ONa—CH$_3$OH (1.0 ml; 4.375 mmol) all at once. The mixture immediately afforded a clear solution and the solution was warmed at reflux temperature for 20 minutes followed by stirring at room temperature for 30 minutes. The mixture was further stirred at 10° C. for 30 minutes and the separated solid was collected by filtration; washed with cold methanol (1×10 ml) and air-dried. This material was crystallized from 1% aqueous ethanol to yield pure 10b (1.16 g; 72%); m.p. 217–20° C. (softens), solidifies and does not melt below 290° C. [lit. m.p. 210–15° C. (softens) and then solidifies and turns brown]. $^1$H NMR (DMSO-d$_6$): δ 8.33 (S, 1H, C$_8$—H), 7.76 (S, 2H, D$_2$O-exchangeable, NH$_2$), 6.25 (t, 1H, peak width 14.0 Hz, C'$_1$—H). Analysis calculated for C$_{10}$H$_{12}$ClN$_5$O$_3$ (285.69): C, 42.04; H, 4.23; N, 24.51; Cl, 12.41. Found: C, 42.01; H, 4.27; N, 24.42 and Cl, 12.49.

EXAMPLE 3

6-Heptanoylamido-9-(3-deoxy-2,5-di-O-benzoyl-β-D-erythropentofuranosyl)purine 1. 6-Heptanoylamidopurine 1 (2.47 g; 10 mmol) was coupled with the 2,5-di-O-benzoyl-3-deoxy-β-D- or L-erythro-pentofuranosyl chloride (3.60 g; 10 mmol) as described for example 1 except the reaction mixture was warmed at reflux temperature for 6 h to obtain after silica gel column purification, the title compound 2.07 g (37%); m.p. 72–74° C. $^1$HNMR (CDCl$_3$): δ 9.07 (br s, 1H, NH), 8.63 (S, 1H, C$_8$—H), 8.22 (S, 1H, C$_2$—H), 6.25 (d, 1H, J$_{1,2}$=1.2 Hz; C'$_1$—H). Analysis calculated for C$_{31}$H$_{33}$N$_5$O$_6$ (571.629): C, 65.13; H, 5.81; N, 12.25. Found: C, 64.90; H, 5.80; N, 11.73.

6-Amino-9-(3-deoxy-β-D-erythropentofuranosyl) purine (3'-Deoxyadenosine; cordycepin) 11a 2. A suspension of 6-heptanoylamido-9-(3-deoxy) pentofuranosyl purine (product of 3a; 1.8 g; 3.15 mmol) was deblocked with sodium methoxide-methanol as described for example 1 to obtain 3-deoxyadenosine. The crude product was crystallized from boiling water to obtain pure 3-deoxyadenosine 11a (0.59 g; 75%) m.p. 224–225° C. [Lit. m.p. 224–225° C. and all other physiochemical properties of the title 3-deoxyadenosine product are identical with those reported in the literature].

EXAMPLE 4

2-Chloro-6-heptanoylamido-9-(3-deoxy-2,5-di-O-benzoyl-β-D-erythro-pentofuranosyl)purine a. 2-chloro-6-heptanoylamido purine 2 (2.0 g; 7 mmol) was coupled with 2,5-di-O-benzoyl-3-deoxy-β-D-erythro-pentofuranosyl chloride (2.55 g; 7.1 mmol) as described for example 2 except the reaction mixture was warmed at reflux temperature for 4 h to obtain after silica gel column purification, the title compound 1.76 g (41%) m.p. 70–72° C. $^1$H NMR (CDCl$_3$): δ 8.65 (br s, 1H, NH), 8.16 (S, 1H, C$_8$—H), 6.21 (d, 1H, J$_{1,2}$=1.6 Hz, C'$_1$—H). Analysis calculated for C$_{31}$H$_{32}$N$_5$ClO$_6$(606.077): C,61.43; H, 5.32; N, 11.55; Cl, 5.84. Found: C, 61.42; H, 5.37, N, 11.21 and Cl, 5.59.

2-Chloro-6-amino-9-(3-deoxy-β-D-erythro-pentofuranosyl)purine (2-chloro-3'-deoxyadenosine). 11b b. A suspension of 2-chloro-6-heptanoylamido-9-3-deoxy-pentofuranosyl purine (product of 4a; 1.7 g; 2.8 mmol) was treated with sodium methoxide-methanol as described for example 2 to obtain the 2-chloro-3'-deoxyadenosine 11b (0.572; 72%) m.p. 208–210° C. $^1$H NMR (DMSO-d$_6$): δ 8.38 (S, 1H, C$_8$—H), 7.81 (br s, 2H, D$_2$O-exchangeable, NH$_2$), 5.80 (d, 1H, J=2.4 Hz,C'$_1$—H) 2.21 and 1.90 (m, 1H each, C'$_3$—H). Analysis calculated for C$_{10}$H$_{12}$ClN$_5$O$_3$ (285.67): C, 42.04; H, 4.23; N, 24.51; Cl, 12.41 Found: C, 42.14; H, 4.30, N, 24.35 and Cl, 12.48.

EXAMPLE 5

6-Heptanoylamido-9-(2'-deoxy-2'-fluoro-3,5-di-O-benzoyl-β-D-arabinofuranosyl)-9H-purine a. 6-Heptanoylamido purine 1 (2.47 g; 10 mmol) was coupled with 3,5-di-O-benzoyl-2-deoxy-2-fluoro-α-D- or L-arabinofuranoyl bromide (4.44 g; 10 mmol) as described for example 3 to obtain after silica gel column purification, the title blocked nucleoside 3.04 g (51%) m.p. 89–91° C. $^1$H NMR (CDCl$_3$): δ 9.25 (br s, 1H, NH), 8.73 (S, 1H, C$_2$—H), 8.35 (d, 1H, J$_8$,F=3.3 Hz, C$_8$—H) 6.69 (dd, 1H, J=19.8, 2.7 Hz, C'$_1$—H), Analysis calculated for C$_{31}$H$_{32}$FN$_5$O$_6$ (589.627): C, 62.94; H, 5.47; N, 11.88; F, 3.22. Found: C, 62.46; H, 5.54; N, 11.78 and F, 3.13.

6-Amino-9-(2'-deoxy-2'-fluoro-β-D-arabinofuranosyl)-9H-purine 12a (2'-deoxy-2'-β-fluoroadenosine)

b. A suspension of 6-heptanoylamido-9-2-deoxy-2-fluoro-β-D- or L-arabinofuranosyl purine (product of 5a; 2.72 g; 4.5 mmol) was treated with sodium methoxide-methanol as descried for example 1 to obtain the 2'-deoxy-2'-β-fluoroadenosine 12a (1.01 g; 81%).m.p. 233–234° C. $^1$H NMR (DMSO-d$_6$); δ 8.23 (d, 1H, J$_8$, F=1.2 Hz, C$_8$—H), 8.14 (S, 1H, C$_2$—H), 7.36 (br s, 2H, D$_2$O-exchangeable, NH$_2$), 6.39 (dd, 1H, J=14.7 and 4.2 Hz, C'$_1$—H). Analysis calculated for C$_{10}$H$_{12}$FN$_5$O$_3$ (269.24): C, 44.61; H, 4.46; N, 26.02, F, 7.06. Found: C, 44.79; H, 4.55; N, 26.20 and F, 6.75.

EXAMPLE 6

2-Chloro-6-heptanoylamido-9-(2-deoxy-2-fluoro-3,5-di-O-benzoyl-β-D-arabinofuranosyl)-9H-purine a. 2-Chloro-6-heptanoylamido purine 2 (5.0 g; 17.8 mmol) was coupled with 3,5-di-O-benzoyl-2-deoxy-2-fluoro-α-D- or L-arabinofuranosyl bromide (7.86 g; 17.85 mmol) as described for example 4 to obtain, after silica gel column purification, the title blocked nucleoside 6.0 g (54%) as a foam suitable for deblocking. A small portion of the foam was crystallized from ethanol to obtain a white solid; m.p. softens at 85° C. and melts at 95–98° C. $^1$HNMR (CDCl$_3$): δ 8.75 (br s, 1H, NH), 8.25 (d, 1H, J$_8$, F=3.5 Hz C$_8$—H), 6.61 (dd, 1H, J=19.5 and 2.0H$_2$, C'$_1$—H).

2-chloro-9-(2'-deoxy-2'-fluoro-β-D-arabinofuranosyl)-9H-purine-6-amine(Clofarabine) 12b b. A suspension of 2-chloro-6-heptanoylamindo-9-(2-deoxy-2-fluoro)-β-D-arabinofuranosyl purine (product of 6a; 14.3 g; 22.91 mmol) was treated with sodium methoxide-methanol as described for example 2 to obtain the crude Clofarabine. This material was crystallized twice from boiling 95% ethanol-water to obtain pure Clofarabine 12b (5.0 g; 60%); m.p. 225–227° C.; $^1$H NMR (DMSO-d$_6$): δ 8.26 (d, 1H, J$_8$, F=1.6 H$_2$, C$_8$—H), 7.89 (br s, 2H, D$_2$O-exchangeable, NH$_2$), 6.30 (dd, 1H, J=18.0 and 4.8 Hz, C'$_1$—H). Analysis calculated for C$_{10}$H$_{11}$ClFN$_5$O$_3$·¼C$_2$H$_5$OH (315.18): C. 40.00; H, 3.89; N, 22.22; Cl, 11.24; F, 6.03. Found: C, 39.50; H, 3.88 N, 21.98; Cl, 10.96 and F, 6.21.

EXAMPLE 7

6-Heptanoylamido-9-(2',3'-dideoxy-2'-fluoro-5-O-p-toluoyl-β-D-arabinofuranosyl)purine a. 6-Heptanoylamido purine 1 (2.47 g; 10 mmol) was coupled with 2,3-dideoxy-2-β-fluoro-5-O-p-toluoyl-chloride (2.9 g; 10 mmol) as described for example 3 to obtain, after silica gel column purification, the title blocked nucleoside. The blocked nucleoside was crystallized from methanol to obtain 2.08 g (43%) of product m.p. 151–152° C. $^1$H NMR (CDCl$_3$): δ 8.74 (br S, 1H, NH) 8.61 (S, 1H, C$_2$—H), 8.25 (d, 1H, J$_8$, F=2.0 Hz, C$_8$—H), 6.34 (dd, 1H, J=2.8 and 20.0 Hz, C'$_1$—H). Analysis calculated for C$_{25}$H$_{30}$FN$_5$O$_4$ (483.54): C, 62.09; H, 6.25; N, 14.48; F, 3.92. Found: C, 62.29; H, 6.19; N, 14.49 and F, 3.49.

9-(2,3-Dideoxy-2-fluoro-β-D-threo-pentofuranosyl) adenine (2'-F-ddara-A, 13a)

b. A suspension of 6-heptanoylamido-2'-3'-dideoxy-2'-fluoro-5-O-toluoyl purine (product of 7a; 1.90 g; 3.93 mmol) was treated with sodium methoxide-methanol as described for example 1 to obtain crude 2'-F-dd-ara-A. This material was crystallized from 20% aq-ethanol to obtain pure F-dd-ara-A 13a (0.81 g; 81%); m.p. 226–227° C. $^1$H NMR (DMSO-d$_6$): δ 8.27 (d, 1H, J$_8$, F=2 Hz, H-8), 8.17 (S, 1H, C$_2$—H), 7.37 (br s, 2H, D$_2$O-exchangeable, NH$_2$), 6.32 (dd, 1H, J=16.8 and 3.6 Hz, H-1'). Analysis calculated for C$_{10}$H$_{12}$FN$_5$O$_2$ (253.23): C, 47.73; H, 4.78; N, 27.66; F, 7.50. Found: C, 47.54; H, 4.86; N, 27.55 and F, 7.31.

EXAMPLE 8

2-Chloro-6-heptanoylamido-9-(2',3'-dideoxy-2'-fluoro-5-O-p-toluoyl-β-D-arabinofuranosyl)purine a. 2-Chloro-6-heptanoylamido purine 2 (5.62 g; 20 mmol) was coupled with 2',3'-dideoxy-2'-β-fluoro-5-O-p-toluoyl chloride (5.8 g; 20 mmol) as described for example 4 to obtain after silica gel column purification the title blocked nucleoside; crystallized from methanol to obtain 2.49 g (24.3%) of product m.p. 118–120° C. $^1$H NMR (CDCl$_3$): δ 9.21 (br s, 1H, NH) 8.36 (d, 1H, J$_8$, F=2.8 Hz; C$_8$—H), 6.35 (dd, 1H, J=17.2 and 2.8 Hz; C'$_1$—H). Analysis calculated for C$_{25}$H$_{29}$ClFN$_5$O$_4$ (517.98): C 57.96; H, 5.64, N, 13.51; F, 3.66; Cl, 6.84. Found: C, 57.74; H, 5.63; N, 12.96 Cl, 6.79; and F, 3.66.

2-Chloro-9-(2,3-dideoxy-2-fluoro-β-D-threo-pentofuranosyl)adenine (2-chloro-2'-F-ddaraA) 13b b. A suspension of 2-chloro-6-heptanoylamido-2',3'-dideoxy-2'-fluoro-5-O-toluoyl purine (product of 8a; 2.07 g; 4 mmol) was treated with sodium methoxide-methanol, as described for example 2 to obtain the crude product; crystallized from 5% aqueous methanol to obtain pure product 13b (0.96 g; 84%); m.p. 212–214° C. $^1$H NMR (DMSO-d$_6$): δ 8.3 (d, 1H, J$_8$, F=2. Hz,C$_8$—H); 7.9 (br s, 2H, D$_2$O exchangeable, NH$_2$); 6.248 (dd, 1H, J=16.0 and 4.0 Hz; C'$_1$—H). Analysis calculated for C$_{10}$H$_{11}$FClN$_5$O$_2$ (287.681): C, 41.75; H, 3.85; N, 24.34; F, 6.60; Cl, 12.32. Found: C, 41.98; H, 4.00; N, 24.40; F, 6.24 and Cl, 12.21.

EXAMPLE 9

2-Chloro-6-heptanoylamidopurine(2)

6-Amino-2-chloropurine (2.37 g, 14 mmol) was suspended in dry xylene (5 mL), and heptanoic anhydride (4.0 mL, 15.26 mmol) was added to the suspension under nitrogen atmosphere with magnetic stirring. The mixture was warmed at reflux temperature for 2 h and concentrated in vacuo (high vacuum, 60° C. water bath) to a semisolid mass. Fresh heptanoic anhydride (4.0 mL, 15.26 mmol) was added to the residue and the mixture was heated with stirring in an oil bath (210° C.). At this point, a clear orange solution was observed (internal temperature 205–207° C.). The clear solution was rapidly cooled in an ice-bath (2–5° C.) with magnetic stirring. Methanol (30 mL) was added to the mixture (internal temperature 55° C.) and stirring (ice-bath) was continued for an additional 30 min. A solid separated that was collected by filtration, washed with methanol (1×10 mL) followed with diethyl ether (2×20 mL). The solid was dried at 70° C./0.3 mm Hg for 3 h to give 3.01 g (76%) of 2 as off-white solid, mp 269–270° C. $R_f$ 0.82 (20% methanol-methylene chloride). $^1$H NMR (DMSO-d$_6$): δ 12.32 (s, 1H, D$_2$O-exchangeable, NH), 11.47 (s, 1H, D$_2$O-exchangeable, NH), 8.413 (s, 1H, C$_8$—H), 2.51 (t, 2H, CH$_2$), 1.60 (m, 2H, CH$_2$), 1.254 (m, 6H, CH$_2$), 0.83 (6, 3H, CH$_3$).

2-Deoxy-3,5-di-O-p-toluoyl-α-D-ribofuranosyl chloride

2-Deoxy-D-ribose (24.2 g, 0.2 mol) was dissolved in anhydrous methanol (486 mL). 1% Methanolic HCl (54 mL, prepared by bubbling anhydrous HCl in methanol) was added and the vessel was sealed and was allowed to stand sealed for 15 minutes to form the methyl glycoside. Silver carbonate (10.0 g) was added. The mixture was shaken well and then filtered. The filtrate was concentrated in vacuo (aspirator, 30° C.) to an oil. Dry pyridine was added (2×10 mL) and the solution was concentrated in vacuo and then placed under high vacuum 30° C./0.3 mmHg for 1 h to give crude methyl glycoside (ca. 36 g). The glycoside was dissolved in dry pyridine (160 mL) and the solution was cooled to 3–5° C. (ice-water bath). p-Toluoyl chloride (68 g, 0.44 mol) was added dropwise while maintaining the temperature below 20° C. After the addition was complete, the mixture was allowed to stand at room temperature overnight. The next day, ice-cold water (600 mL) was added and the mixture was extracted with ether (2×400 mL) The combined ether extracts were washed successively with water (2×200 mL), dilute sulfuric acid (2.5 N, 2×300 mL), saturated sodium bicarbonate solution (2×400 mL), and dried (MgSO$_4$). The mixture was filtered and the filtrate was concentrated at 30° C. in vacuo (aspirator, then 0.3 mm Hg for 1 h) to give 1-O-methyl-3,5-di-O-(p-toluoyl)-2-deoxy-D-ribofuranoside as a yellow syrup (ca. 90 g). The syrup was dissolved in glacial acetic acid (60 mL) and then added to acetic acid saturated with HCl gas (160 mL). While maintaining the temperature at 10° C., anhydrous HCl was passed into the solution for 10 minutes (the solution turned to a thick crystalline paste). The mixture was diluted with anhydrous ether (100 mL), filtered, and the resulting solid was recrystallized from toluene (500 mL) and dried in a vacuum desiccator over soda lime and P$_2$O$_5$ to give pure product, 44.0 g (51%), mp 117–119° C.

2-Chloro-6-heptanoylamido-9-(2-deoxy-3,5-di-O-p-toluoyl-β-D-erythropentofuranosyl)purine (5)

The amide 2 (3.94 g, 14 mmol) was suspended in dry acetonitrile (60 mL) and the mixture was warmed to 40° C. under nitrogen atmosphere. Sodium hydride (60% in oil, 0.56 g, 14 mmol) was added portionwise over 5 min and the resulting suspension was stirred at room temperature for 30 minutes. Dry, powdered α-chloro sugar (6.0 g, 15.4 mmol) was added portionwise to the mixture with stirring over 10 minutes. Stirring was continued for 2 h 30 min. The reaction mixture was concentrated in vacuo (aspirator, 40° C. water bath) and the residue was partitioned between methylene chloride (200 mL) and water (50 mL). The organic layer was separated and the aqueous layer was extracted with methylene chloride (2×75 mL). The combined organic extract was washed with dilute 1% HCl (1×100 ml), 5% sodium bicarbonate solution (1×100 mL) and brine (1×100 ml), then dried (MgSO$_4$), filtered and concentrated (aspirator, 40° C. water bath) to a semisolid mass. The residue was dried further (high vacuum, 35° C. water bath) for 1 h to give a solid. At this stage it was necessary to remove residual methylene chloride to maximize the yield of blocked nucleoside 5). The solid was triturated with boiling diethyl ether (1×70 mL) and the mixture was then stirred at room temperature for 30 min. The separated solid was collected by filtration to give 4.0 g of solid (air-dried, 10 min). The material was further triturated with boiling ether (1×25 mL) for 10 min, cooled to room temperature and the solid was collected by filtration, and then dried at 50° C./0.3 mm Hg for 2 h to give 3.64 g (41%) of compound 5, mp 128–130° C. $R_f$ 0.55 (40% ethyl acetate-hexanes). $^1$H NMR (DMSO-d$_6$): δ 10.98 (s, 1H, D$_2$O-exchangeable, NH), 8.66 (s, 1H, C$_8$H), 7.93 (dd, 2H, ArH), 7.78 (dd, 2H, ArH), 7.34 (dd, 2H, ArH), 7.253 (dd, 2H, ArH), 6.535 (t, 1 H, J$_1$', 2'=6.9 Hz, C$_1$'—H), 5.776 (m, 1H, C$_3$"—H), 4.575 (m, 2H, C$_5$'OCH$_2$), 4.52 (m, 1H, C$_4$'—H), 3.23 (m, 1H, C$_2$'—H), 2.82 (m, 1H, C$_2$'—H)

2-Chloro-2'-deoxyadenosine (10b)

The blocked nucleoside 5 (3.60 g, 5.68 mmol) was suspended in anhydrous methanol (30 mL) and the mixture was warmed with stirring to 50° C. (internal temp). Sodium methoxide was added to the stirred suspension (25 wt % solution in methanol, 1.0 mL, 4.375 mmol; pH ca. 10.5) and the resulting clear solution became cloudy after stirring at room temperature for 20 min. The solution was stirred under nitrogen atmosphere in an ice cold bath (5–10° C.) for an additional 30 min. The solid was collected by filtration, washed with cold methanol (1×10 mL) and air dried to give 1.28 g.

The material was triturated with boiling ethanol (20 mL) and the mixture was stirred at room temperature for 15 min. The solid was collected by filtration and dried at 70° C./0.3 mm Hg for 3 h to give 2-chloro-2'-deoxyadenosine 6, 1.164 g (72%), mp 220° C. (softens at 210–215° C.). $R_f$ 0.31 (20% methanol-methylene chloride).

The present invention provides the following advantages:

1. The use of protecting groups for a 6-aminopurine ("Adenine derivative") that impart appropriate solubility and bulk to the purine base to afford a protected base such that the protected base is soluble in organic solvents and N$^7$ position is hindered to minimize reaction at that position during coupling with an activated sugar to synthesize 9-β-purine nucleosides.

2. The use of the protected purine base with an appropriate base and solvent to minimize formation of the α-isomer when coupling the protected purine to an activated sugar to form nucleosides.

3. The use of organic soluble, metallic bases in dipolar, aprotic solvents to couple an organic soluble purine base derivative with an activated sugar to form nucleosides 4. The use of a 6-heptanoylamido purine base and potassium hexamethyl disilazide in a solvent tetrahydrofuran to couple the base to an activated sugar to form nucleosides.

5. The synthesis of Cladribine; Clofarabine; Fluoro dideoxy adenosine (FddA); Fludarabine; and Cordycepin.

It is intended that the foregoing description be only illustrative of the present invention and that the present invention be limited only by the hereinafter appended claims.

We claim:

1. A process for producing a protected 9-substituted purine nucleoside (I) of the formula:

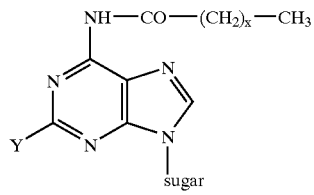

wherein x is 5 to 12 and Y is selected from the group consisting of H, Cl, F, Br, $OCH_3$, $NH_2$ and NHR wherein R is a non-reactive group, and sugar has protected hydroxyl groups which comprises:

reacting in a reaction mixture an anionic 6-substituted purine (II) of the formula:

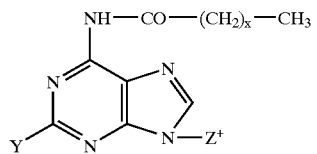

wherein Z is Na or K as a cation,
with a halosugar with protected hydroxyl groups in a non-reactive dipolar aprotic organic solvent for (II) and Y does not react in the process to produce (I), essentially without formation of a 7-position analog.

2. The process of claim 1 wherein x is 5.

3. The process of claim 1 or 2 wherein the halosugar is selected from the group consisting of a pentafuranose, 2-deoxypentofuranose and a substituted 2-deoxypentafuranose substituted with a 1-halo group and with the protected hydroxy groups.

4. The process of claim 1 or 2 wherein the solvent is anhydrous tetrahydrofuran.

5. The process of claim 1 or 2 wherein (II) is produced by reacting a compound (III) of the formula

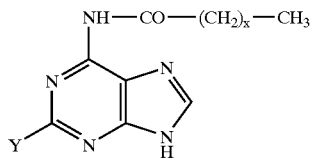

with an organic base comprising K or Na as a cation to provide the 6-substituted purine II in the reaction mixture.

6. The process of claim 5 wherein compound (III) is prepared by reacting a Y-adenine with an anhydride of the formula:

where x is 5 to 12.

7. The process of claim 1 wherein x is 5 to 9.

8. The process of claim 1 wherein the sugar is a 1-halosugar.

9. The process of claim 1 or 2 wherein (II) is produced by reacting a compound III of the formula:

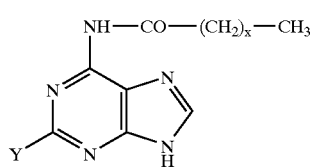

with potassium hexamethyl disalazide (KHMDS) as an organic base to form the potassium cation of (II).

10. The process of claim 1 wherein the sugar in (I) is deprotected and the 6-substituent is hydrolyzed to produce a 6-aminopurine nucleoside in a single pot reaction.

11. The process of claim 10 wherein the 6-aminopurine nucleoside is 2-chloro-2'-F-2'-deoxy-ara-adenosine (Clofarabine).

12. The process of claim 10 wherein the 6-amino purine nucleoside is 2-chloro-2'-F-dideoxy-ara-adenosine.

13. The process of claim 10 wherein the 6-amino-purine nucleoside is 2'-F-dideoxy-ara-adenosine.

14. The process of claim 10 wherein the 6-aminopurine nucleoside is 2-fluoro-ara-adenosine.

15. The process of claim 10 wherein the 6-aminopurine nucleoside is 2-deoxy adenosine.

16. The process of claim 10 wherein the 6-aminopurine nucleoside is 2-chloro-2'-deoxyadenosine (Cladribine).

17. The process of claim 10 wherein the 6-aminopurine nucleoside is 3'-deoxyadenosine.

18. The process of claim 10 wherein the 6-aminopurine nucleoside is 2-chloro-3'-deoxyadenosine.

19. The process of claim 10 wherein the 6-aminopurine nucleoside is 2'-F-2'-deoxy-ara-adenosine.

20. A process for producing a protected 9-substituted purine nucleoside of (I) essentially without formation of 7-position isomers of the formula

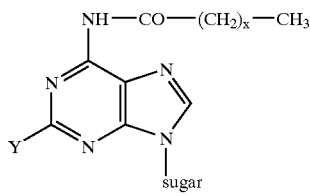

wherein x is 5 to 12 carbon atoms and Y is a group which does not react in the process and sugar has protected hydroxyl groups which comprises:

(a) providing a purine of the formula:

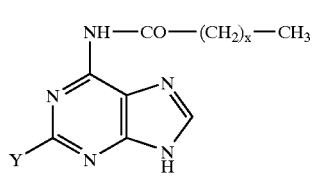

in a reaction mixture with an organic solvent for III;

(b) reacting the purine (III) with potassium or sodium salt of an organic base in the reaction mixture to provide a purine salt of the formula

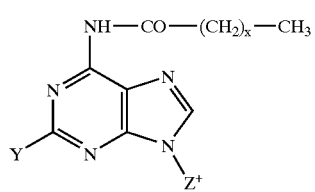

where Z is Na or K as a cation; and (c) reacting in the reaction mixture the purine salt with a halosugar in a solvent for (II) which does not participate in the reaction to produce (I) essentially without formation of the 7-position isomers.

21. The process of claim 20 wherein the organic base is potassium hexamethyl disalazide.

22. The process of claim 20 wherein the organic base is sodium hexamethyl disalazide.

* * * * *

UNITED STATES PATENT AND TRADEMARK OFFICE
CERTIFICATE OF CORRECTION

PATENT NO. : 6,884,880 B2
DATED : April 26, 2005
INVENTOR(S) : Pranab K. Gupta and Stephen A. Munk It is certified that error appears in the above-identified patent and that said Letters Patent is hereby corrected as shown below:

<u>Column 11,</u>
Line 53, "(5.0g; 60%)" should read -- 5.01g; 60%) --.

Signed and Sealed this

Twenty-third Day of August, 2005

JON W. DUDAS
*Director of the United States Patent and Trademark Office*